United States Patent
Martin

(10) Patent No.: US 9,422,701 B2
(45) Date of Patent: Aug. 23, 2016

(54) TOILET WATER SPLASH INHIBITING DEVICE

(71) Applicant: Judy C. Martin, Toronto (CA)

(72) Inventor: Judy C. Martin, Toronto (CA)

(*) Notice: Subject to any disclaimer, the term of this patent is extended or adjusted under 35 U.S.C. 154(b) by 35 days.

(21) Appl. No.: 14/527,431

(22) Filed: Oct. 29, 2014

(65) Prior Publication Data

US 2016/0122991 A1    May 5, 2016

(51) Int. Cl.
*E03D 9/00*   (2006.01)
*E03D 9/02*   (2006.01)
*A61L 9/05*   (2006.01)

(52) U.S. Cl.
CPC ... *E03D 9/00* (2013.01); *A61L 9/05* (2013.01); *E03D 9/005* (2013.01); *E03D 9/007* (2013.01)

(58) Field of Classification Search
None
See application file for complete search history.

(56) References Cited

U.S. PATENT DOCUMENTS

| | | | | |
|---|---|---|---|---|
| 2,801,951 A * | 8/1957 | Cooper, Jr. | ............ | A61K 9/2009 514/162 |
| 3,428,558 A * | 2/1969 | Murphy | ................ | C02F 1/5227 134/22.19 |
| 4,578,207 A | 3/1986 | Holdt et al. | | |
| 5,137,731 A | 8/1992 | Casberg | | |
| 5,759,574 A | 6/1998 | Bothe | | |
| 6,713,441 B1 | 3/2004 | DeSenna et al. | | |
| 7,250,174 B2 * | 7/2007 | Lee | .......................... | A61K 8/22 424/400 |
| 7,563,756 B2 | 7/2009 | Brady | | |
| D650,524 S | 12/2011 | Wilson et al. | | |
| 2002/0187119 A1 | 12/2002 | Greer et al. | | |
| 2013/0323194 A1 * | 12/2013 | Everhart | ................. | A61L 9/044 424/76.6 |

* cited by examiner

*Primary Examiner* — Joseph D Anthony

(57) ABSTRACT

A toilet water splash inhibiting device for inhibit splashing of toilet water during evacuation of waste into a toilet. The device includes a mixture of liquid body soap, baking soda, vinegar, sodium bicarbonate, aspirin, and anhydrous citric acid.

2 Claims, No Drawings

TOILET WATER SPLASH INHIBITING DEVICE

BACKGROUND OF THE DISCLOSURE

1. Field of the Disclosure

The disclosure relates to splash inhibiting devices and more particularly pertains to a new splash inhibiting device for inhibit splashing of toilet water during evacuation of waste into a toilet.

SUMMARY OF THE DISCLOSURE

An embodiment of the disclosure meets the needs presented above by generally comprising a mixture of liquid body soap, baking soda, vinegar, sodium bicarbonate, aspirin, and anhydrous citric acid.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

DESCRIPTION OF THE PREFERRED EMBODIMENT

The toilet water splash inhibiting device generally comprises a mixture combined and formed into a single tablet for depositing into a toilet bowl. The mixture comprises between 25 and 35 milliliters of a liquid body soap. The body soap may be scented and of the type commonly found commercially under various trade names including but not limited to LEVER. The mixture further comprises between 1.5 and 2.5 tablespoons of baking soda provided in powder form. The mixture also comprises between 80 and 100 milliliters of white vinegar. The mixture also comprises sodium bicarbonate, aspirin, and anhydrous citric acid as found together in commercially available anti acid medications in tablet form under the trade name ALKA SELTZER. The mixture comprises between 3 and 5 tablets of the anti-acid medication. The tablets of anti acid medication are crushed to be mixed with the other components of the mixture. The above components are provided in the range of the above described amounts and mixed prior to placement into a form to be dried into a single tablet suitable for individual use.

In use, the single tablet of the mixture is deposited into the toilet bowl whereupon the tablet dissolves into toilet water in the toilet bowl forming a layer of the mixture on a surface of the toilet water. The layer on the surface of the toilet water inhibits splashing of the toilet water and liquid waste deposited into the toilet bowl while a user evacuates waste into the toilet bowl.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A toilet water splash inhibiting device comprising a mixture of between 25 and 35 milliliters of a commercially sold liquid body soap, between 1.5 and 2.5 tablespoons of baking soda, between 80 and 100 milliliters of white vinegar, and sodium bicarbonate, aspirin, and anhydrous citric acid being in amounts equivalent to between 3 and 5 tablets of an effervescent commercially sold anti-acid tablet.

2. The device of claim 1, further comprising said mixture being combined, dried, and formed into a single tablet.

* * * * *